(12) United States Patent
Horton et al.

(10) Patent No.: US 11,090,056 B2
(45) Date of Patent: Aug. 17, 2021

(54) CATHETER ASSEMBLY AND SYSTEMS AND METHODS OF USING SAME

(71) Applicant: APPLIED CARDIOVASCULAR SOLUTIONS, LLC, Austin, TX (US)

(72) Inventors: Rodney Paul Horton, Austin, TX (US); Michael David Horton, Austin, TX (US); Francisco Javier Otero, Austin, TX (US)

(73) Assignee: APPLIED CARDIOVASCULAR SOLUTIONS, LLC, Austin, TX (US)

( * ) Notice: Subject to any disclaimer, the term of this patent is extended or adjusted under 35 U.S.C. 154(b) by 0 days.

(21) Appl. No.: 16/763,617

(22) PCT Filed: Nov. 15, 2018

(86) PCT No.: PCT/US2018/061302
§ 371 (c)(1),
(2) Date: May 13, 2020

(87) PCT Pub. No.: WO2019/099686
PCT Pub. Date: May 23, 2019

(65) Prior Publication Data
US 2020/0360026 A1    Nov. 19, 2020

Related U.S. Application Data

(60) Provisional application No. 62/587,149, filed on Nov. 16, 2017.

(51) Int. Cl.
*A61B 17/12* (2006.01)
*A61B 17/00* (2006.01)

(52) U.S. Cl.
CPC .. *A61B 17/12122* (2013.01); *A61B 17/12136* (2013.01); *A61B 17/12186* (2013.01); *A61B 17/12195* (2013.01); *A61B 2017/00632* (2013.01)

(58) Field of Classification Search
CPC ........ A61B 17/12122; A61B 17/12022; A61B 17/12027; A61B 17/12031; A61B 17/1204; A61B 17/12131; A61B 17/12136; A61B 2017/00632; A61M 25/10; A61M 25/1011; A61M 2025/1013; A61M 2025/1015; A61M 2025/1043; A61M 2025/1052
See application file for complete search history.

(56) References Cited

U.S. PATENT DOCUMENTS

| | | |
|---|---|---|
| 8,142,470 B2 | 3/2012 | Quinn et al. |
| 2010/0286718 A1 | 11/2010 | Kassab et al. |
| 2014/0277070 A1 | 9/2014 | Otero et al. |
| 2016/0089151 A1 | 3/2016 | Siegel et al. |
| 2016/0166242 A1 | 6/2016 | Krishnan |
| 2016/0192911 A1 | 7/2016 | Kessab et al. |

OTHER PUBLICATIONS

International Search Report and the Written Opinion for PCT/US2018/061302 dated Feb. 15, 2019.

*Primary Examiner* — Melanie R Tyson
(74) *Attorney, Agent, or Firm* — Ballard Spahr LLP

(57) ABSTRACT

Devices, systems, and methods for occluding cavities or passageways in a subject, such as the left atrial appendage of a subject's heart. The devices, systems, and methods can be used to decrease the rate of thromboembolic events associated with atrial fibrillation by occluding the left atrial appendage.

21 Claims, 7 Drawing Sheets

CATHETER ASSEMBLY AND SYSTEMS AND METHODS OF USING SAME

CROSS-REFERENCE TO RELATED APPLICATION

This is a U.S. National Phase Application of International Application No. PCT/US2018/061302, filed Nov. 15, 2017, which claims priority to and the benefit of the filing date of U.S. Provisional Patent Application No. 62/587,149, filed on Nov. 16, 2017, which applications are hereby incorporated herein by reference in [its] their [entirety] entireties.

FIELD

This disclosure relates to devices, systems, and methods for occluding cavities or passageways in a subject, and in particular to catheter assemblies for occluding cavities or passageways in the cardiovascular system of a subject.

BACKGROUND

Embolic stroke is a leading cause of death and disability among adults. The most common cause of embolic stroke emanating from the heart is thrombus (i.e., clotting) formation due to atrial fibrillation. Atrial fibrillation is an arrhythmia of the heart that results in a rapid and chaotic heartbeat, producing decreased cardiac output and leading to irregular and turbulent blood flow in the vascular system.

For patients who develop atrial thrombus from atrial fibrillation, clot formation typically occurs in the left atrial appendage (LAA) of the heart. The LAA is a cavity formed within the lateral wall of the left atrium between the mitral valve and the root of the left pulmonary vein. The LAA normally contracts in conjunction with the rest of the left atrium during the cardiac cycle; however in the case of patients suffering from atrial fibrillation, the LAA often fails to contract with any vigor. As a consequence, blood can stagnate within the LAA, resulting in thrombus formation, which then becomes a risk as the irregular contraction of the LAA may force the clot to travel out of the appendage and into the brain, leading to a stroke.

Elimination or containment of thrombus formed within the LAA offers the potential to significantly reduce the incidence of stroke in patients suffering from AF. Pharmacological therapies, for example the oral or systemic administration of anticoagulants such as warfarin, are often undesirable or unsuccessful due to medication side effects (e.g., hemorrhage), interactions with foods and other drugs, and lack of patient compliance. Other treatment options include thoracoscopic surgical removal and ligation of the LAA, but these procedures also have several drawbacks including exclusion of high surgical risk candidates, high morbidity, mortality risk, infection, and others.

Less invasive approaches to LAA occlusion have been developed in recent years, such as intravascular catheters for delivery of an occluding material to the LAA. These devices, however, have drawbacks such as insufficient sealing at the ostium, insufficient delivery of occluding material, inadequate fixation of the device, poor hemodynamic design leading to excessive thrombo-emboli in the atrium, and other drawbacks described in more detail below. Accordingly, there is a need for devices, systems, and methods that address one or more of these deficiencies.

SUMMARY

Described herein, in various aspects, is a catheter assembly. The catheter assembly can comprise a first catheter body having a proximal end portion, a distal end portion having a distal tip, and a wall that circumferentially encloses a primary opening. The first catheter body can further comprise at least one inflation channel within the wall of the first catheter body. The primary opening of the first catheter body can extend along an entire length of the first catheter body. The catheter assembly can also comprise a first balloon coupled to the distal end portion of the first catheter body and positioned in fluid communication with the at least one inflation channel of the first catheter body. The first balloon can enclose an interior space, and the first catheter body can extend through the interior space of the first balloon in a proximal-to-distal direction such that at least the distal tip of the first catheter body is positioned distal of the first balloon.

The catheter assembly can also comprise a second catheter body partially received within the primary opening of, and selectively moveable relative to, the first catheter body. The second catheter body can include a proximal end portion, a distal end portion having a tip, and a wall that circumferentially encloses a primary opening. The second catheter body can further comprise at least one inflation channel within the wall of the second catheter body. The primary opening of the second catheter body can extend along an entire length of the second catheter body. The catheter assembly can further include a second balloon coupled to the distal end portion of the second catheter body and positioned in fluid communication with the at least one inflation channel of the second catheter body. The second balloon can enclose an interior space, and the second catheter body can extend through the interior space of the second balloon in the proximal-to-distal direction such that at least the distal tip of the second catheter body is positioned distal of the second balloon.

Additionally, the catheter assembly can comprise a third catheter body partially received within the primary opening of, and selectively moveable relative to, the second catheter body. The third catheter body can include a proximal end portion, a distal end portion, and a wall structure that defines at least one injection channel extending from the proximal end portion toward the distal end portion. The distal end portion of the third catheter body can further comprise at least one outlet opening positioned in fluid communication with the at least one injection channel.

Disclosed herein, in further aspects, is a method for delivering at least one injectable material to a selected delivery site through the at least one outlet opening of the third catheter body. The method can include the steps of: deploying the catheter assembly disclosed herein; selectively inflating the first balloon to occlude a first opening; selectively advancing the second catheter body relative to the first catheter body; selectively inflating the second balloon to occlude a second opening; selectively advancing the third catheter body relative to the second catheter body; selectively delivering at least one injectable material to the at least one injection channel of the third catheter body; and delivering the at least one injectable material to a selected delivery site through the at least one outlet opening of the third catheter body.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

These and other features of the preferred embodiments of the invention will become more apparent in the detailed description in which reference is made to the appended drawings.

The patent or application file contains at least one drawing executed in color. Copies of this patent or patent application publication with color drawings will be provided by the Office upon request and payment of the necessary fee.

DETAILED DESCRIPTION

The present invention can be understood more readily by reference to the following detailed description and appendix, which include examples, drawings, and claims. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "an inflation channel" can include two or more such inflation channels unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," it is contemplated that values within up to 15%, up to 10%, or up to 5% (above or below) of the particularly stated value can be included within the scope of those aspects.

As used herein, the terms "optional" or "optionally" mean that the subsequently described event or circumstance may or may not occur, and that the description includes instances where said event or circumstance occurs and instances where it does not.

As used herein, the term "subject" refers to both human and animal subjects.

As used herein, the term "balloon" refers to any inflatable (e.g., selectively inflatable) element that can be introduced into a passageway, cavity, opening, or vessel of a subject and expanded (by way of gas, liquid, or other fluid) to seal against an opening or passageway within the body of a subject, to hold components of the disclosed catheter assembly in place in a desired location inside of the subject's body, and/or to expand a partly closed or obstructed bodily passageway, cavity, opening, or vessel.

Described herein, with references to FIGS. 1A-11, is a catheter assembly 10 for occluding cavities or passageways in a subject, and in particular, to occluding cavities or passageways such as the left atrial appendage (LAA) of a subject's heart. Although many of the embodiments are described below with respect to devices, systems, and methods for occlusion of the LAA, it is contemplated that other applications in addition to those described herein are within the scope of the present technology. As described in further detail herein, the disclosed catheter assembly 10 can comprise three catheter bodies 12, 40, 70 and two balloons 30, 60 which cooperate with each other to deliver at least one injectable material 200 to the LAA of a subject's heart in a manner such that complete closure of the LAA is achieved.

Figures 1A, 1B, 1C, 1D:
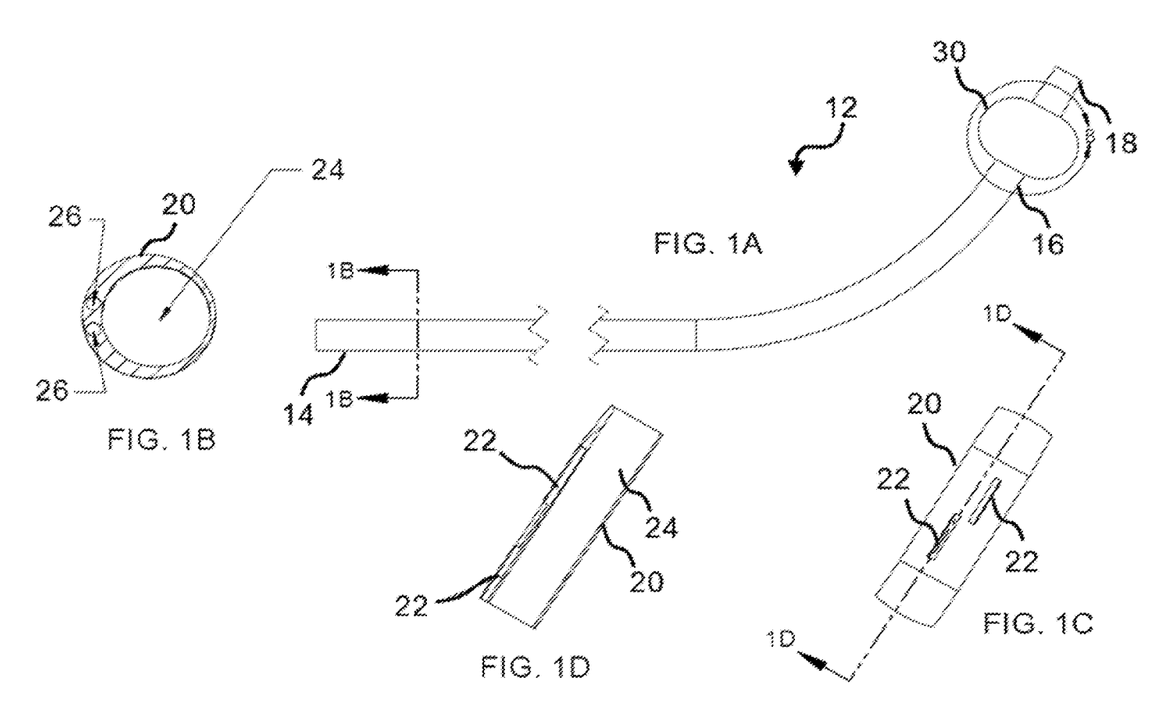
FIG. 1A is a schematic illustration of an exemplary first catheter body and first balloon, as described herein. As shown, the first catheter body can have a proximal end portion, a distal end portion having a tip, and a wall that circumferentially encloses a primary opening.
FIG. 1B is a cross-sectional side view of the first catheter body taken along line 1B-1B of FIG. 1A, as described herein. As shown, the first catheter body can have at least one inflation channel within the wall of the first catheter body. The primary opening of the first catheter body can extend an entire length of the first catheter body.
FIG. 1C is a close-up view of a portion of the first catheter body of FIG. 1A showing at least one outlet opening defined therein to provide fluid communication between the at least one inflation channel and the interior space of the first balloon, as described herein.
FIG. 1D is a cross-sectional side view of the portion of the first catheter body of FIG. 1C taken along line 1D-1D, as described herein.

In exemplary aspects, as shown in FIG. 1A, the catheter assembly 10 can comprise a first catheter body 12 that includes a proximal end portion 14, a distal end portion 16 having a distal tip 18, and a wall 20 that circumferentially encloses a primary opening 22. In these aspects, the primary opening 22 of the first catheter body 12 can extend along an entire length of the first catheter body. As shown in FIG. 1B, the first catheter body 12 can comprise at least one inflation channel 26 (optionally, a plurality of inflation channels, such as, for example, two inflation channels) within the wall 20 of the first catheter body. In further aspects, the catheter assembly 10 can comprise a first balloon 30 that can be coupled to the distal end portion 16 of the first catheter body 12 and positioned in fluid communication with the at least one inflation channel 26 of the first catheter body. In these aspects, the first balloon 30 can enclose an interior space 32. As shown in FIGS. 1C and 1D, the wall 20 of the first catheter body 12 can define at least one outlet opening 22 (optionally, a plurality of outlet openings) to provide fluid communication between the at least one inflation channel 26 and the interior space 32 of the first balloon 30. In some aspects, the each outlet opening can be in fluid communication with a respective inflation channel. In additional aspects, the plurality of outlet openings can be circumferentially spaced, axially spaced (in a distal or proximal direction), or both circumferentially and axially spaced in a staggered configuration. In further aspects, the first catheter body 12 can extend through the interior space 32 of the first balloon 30 in a proximal-to-distal direction such that at least the distal tip 18 of the first catheter body 12 is positioned distal of the first balloon 30.

Figures 2A, 2B, 2C:
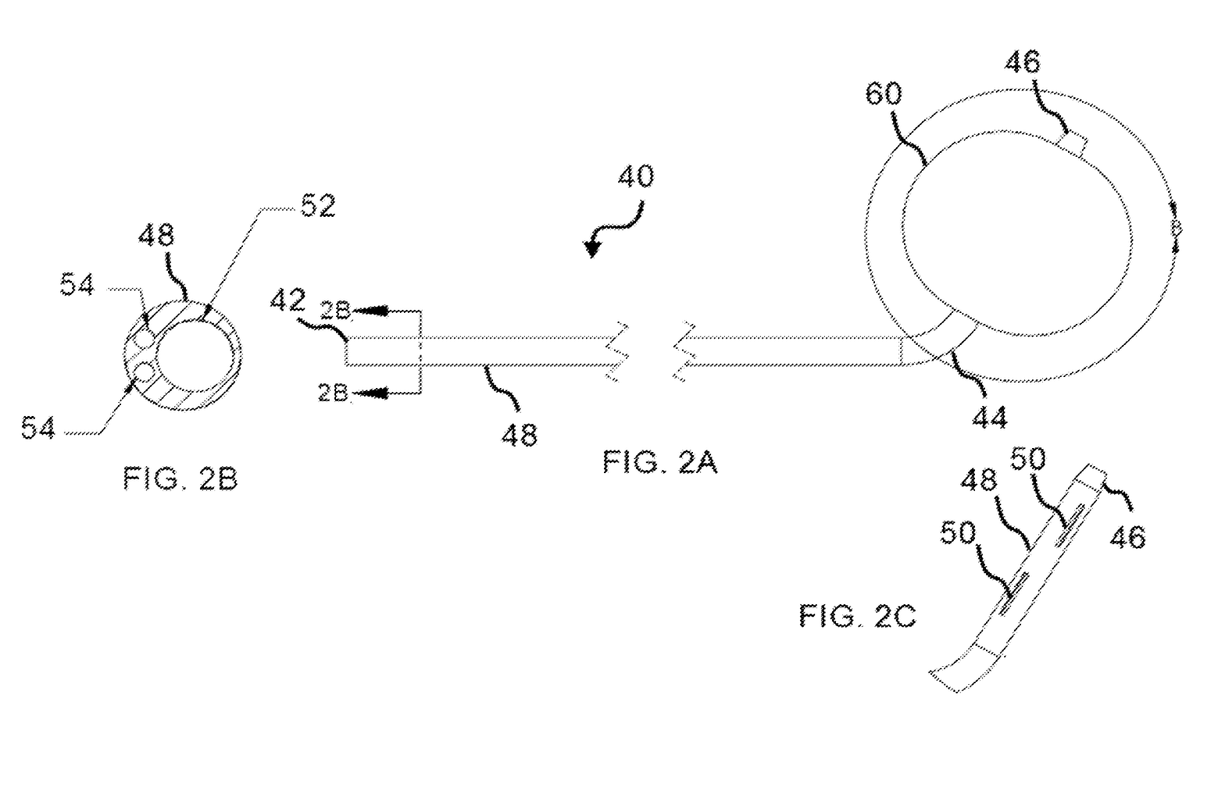
FIG. 2A is a schematic illustration of an exemplary second catheter body and second balloon, as described herein. As shown, the second catheter body can have a proximal end portion, a distal end portion having a tip, and a wall that circumferentially encloses a primary opening.
FIG. 2B is a cross-sectional side view of the second catheter body taken along line 2B-2B of FIG. 2A, as described herein. As shown, the second catheter body can have at least one inflation channel within the wall of the second catheter body, and the primary opening of the second catheter body can extend an entire length of the second catheter body.
FIG. 2C is a close-up view of a portion of the second catheter body of FIG. 2A showing at least one outlet opening defined therein to provide fluid communication between the at least one inflation channel and the interior space of the second balloon, as described herein.

Referring to FIGS. 2A-2C, the catheter assembly 10 can comprise a second catheter body 40 that can be partially received within the primary opening 24 of, and selectively moveable relative to, the first catheter body 12. Optionally, in some aspects, it is contemplated that the second catheter body 40 can be selectively retractable relative to the first catheter body 12. In further optional aspects, it is contemplated that the first and second catheter bodies 12, 40 can be selectively lockable to maintain a desired position and orientation of the second catheter body 40 relative to the first catheter body 12. Optionally, in exemplary aspects, it is contemplated that the proximal ends of the first and second catheter bodies 12, 40 can be provided with Tuohy-type locking mechanisms as are known in the art (e.g., Tuohy-Borst adapters) to use friction to lock the first catheter body to the second catheter body. However, it is contemplated that any suitable locking mechanism as is known in the art can be used for this purpose. In additional aspects and as shown in FIG. 2A, the second catheter body 40 can include a proximal end portion 42, a distal end portion 44 having a distal tip 46, and a wall 48 that circumferentially encloses a primary opening 52 of the second catheter body 40. The primary opening 52 of the second catheter body 40 can extend along an entire length of the second catheter body. As shown in FIG. 2B, the second catheter body 40 can further comprises at least one inflation channel 54 (optionally, a plurality of inflation channels, such as for example, two inflation channels) within the wall 48 of the second catheter body 40.

Figure 4:
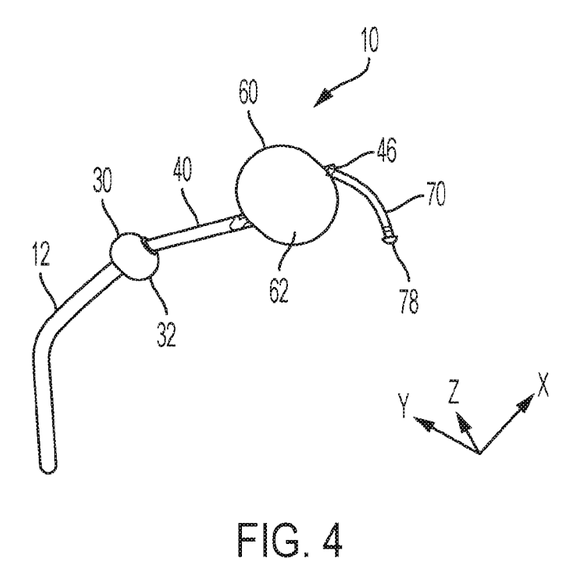
FIG. 4 is a perspective view of an exemplary catheter assembly, as described herein.
Figure 5:
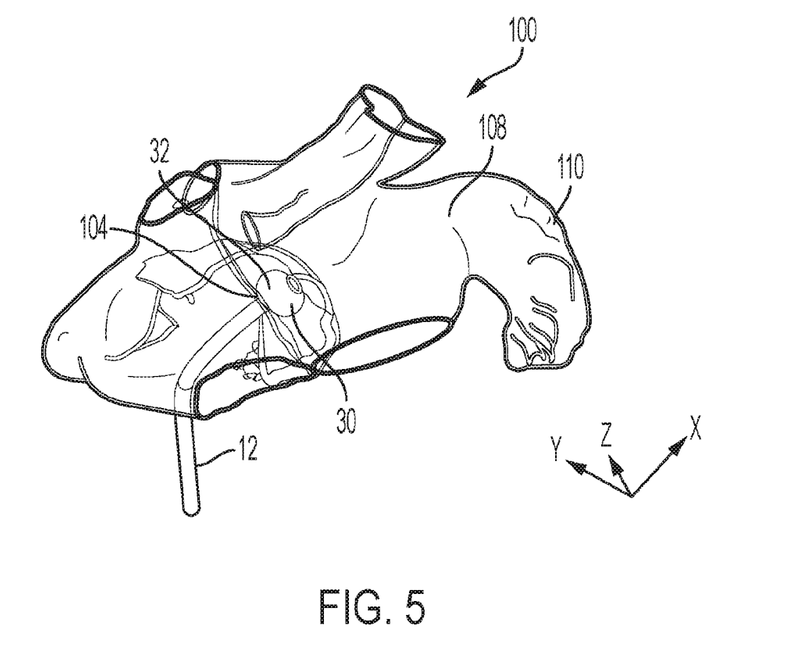
FIG. 5 is a perspective view depicting an exemplary catheter assembly, showing a first catheter body advanced through an inter-atrial septum of a heart and a first balloon inflated and positioned on a left atrial septal side of the inter-atrial septum of the heart, as described herein.

In further aspects, the catheter assembly 10 can comprise a second balloon 60 that can be coupled to the distal end portion 44 of the second catheter body 40 and positioned in fluid communication with the at least one inflation channel 54 of the second catheter body. In these aspects, the second balloon 60 can enclose an interior space 62. As shown in FIG. 2C, the wall 48 of the second catheter body 40 can define at least one outlet opening 50 (optionally, a plurality of outlet openings) to provide fluid communication between the at least one inflation channel 54 and the interior space 62 of the second balloon. In some aspects, the each outlet opening 50 can be in fluid communication with a respective inflation channel 54. In additional aspects, the plurality of outlet openings 50 can be circumferentially spaced, axially spaced (in a distal or proximal direction), or both circumferentially and axially spaced in a staggered configuration. In further aspects, the second catheter body 40 can extend through the interior space 62 of the second balloon 60 in the proximal-to-distal direction such that at least the distal tip 46 of the second catheter body 40 is positioned distal of the second balloon 60. As depicted in FIG. 4, it is contemplated that when in an inflated position (e.g., a fully inflated position), the second balloon 60 can be larger (e.g., have a larger diameter) than the first balloon 30 (when the first balloon is also in an inflated or fully inflated position). Optionally, in exemplary aspects, it is contemplated that the maximum inflated diameter of the first balloon 30 can range from about 10 mm to about 20 mm or, more preferably, be about 15 mm. Optionally, in additional aspects, it is contemplated that the maximum inflated diameter of the second balloon 60 can range from about 30 mm to about 50 mm or from about 35 mm to about 45 mm or, more preferably, be about 40 mm. Optionally, in further exemplary aspects, it is contemplated that the first and second balloons are not spherical. For example, it is contemplated that each balloon can have an axial length (relative to the length of the catheter bodies) that is less than its maximum inflated diameter.

Figure 3A:
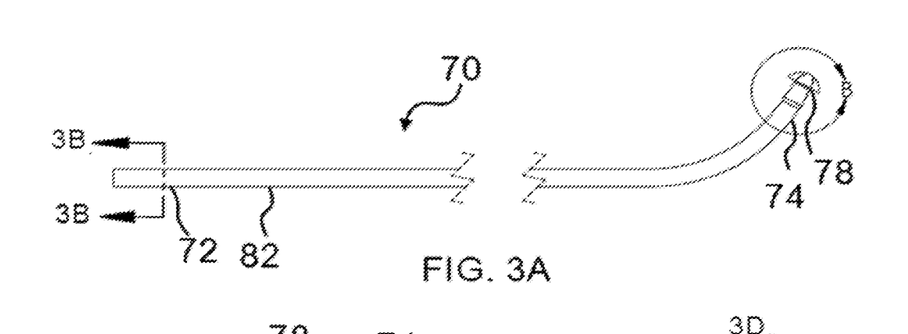
FIG. 3A is a schematic illustration of an exemplary third catheter body, as described herein. As shown, the third catheter body can include a proximal end portion, a distal end portion, and a wall structure that defines at least one injection channel extending from the proximal end portion toward the distal end portion.
Figure 3B:
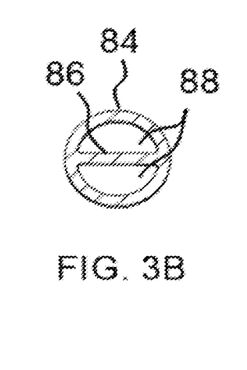
FIG. 3B is a cross-sectional side view of the third catheter body taken along line 3B-3B of FIG. 3A, which shows the least one injection channel.
Figure 3C:
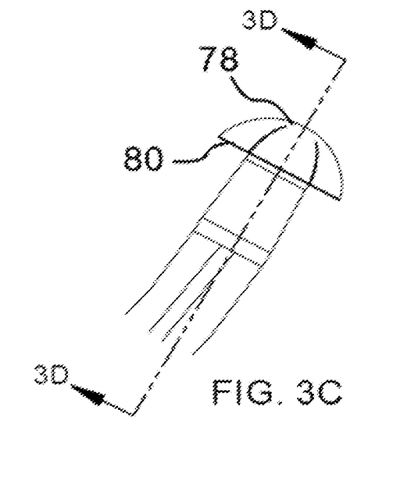
FIG. 3C is a close-up view of the distal end portion of the third catheter body of FIG. 3A, as described herein.
Figure 3D:
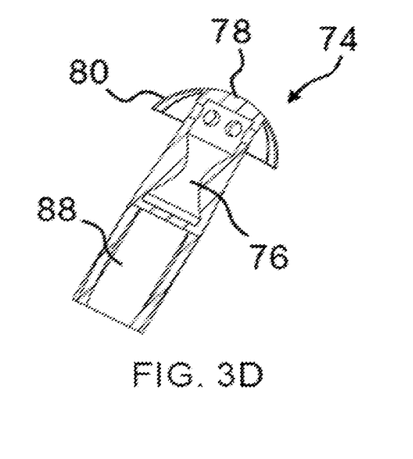
FIG. 3D is a cross-sectional side view of the distal end portion taken along line 3D-3D of FIG. 3C. As shown and described herein, the distal end portion can at least one outlet opening positioned in fluid communication with the at least one injection channel.

Referring to FIGS. 3A-3D, the catheter assembly 10 can comprise a third catheter body 70 that can be partially received within the primary opening 52 of, and selectively moveable relative to, the second catheter body 40. Optionally, in some aspects, the third catheter body 70 can be selectively retractable relative to the second catheter body 40. It is contemplated that, when the third catheter body is fully retracted, the third catheter body 70 can be fully received within the primary opening 52 of the second catheter body 40. In these aspects, as shown in FIG. 3A, the third catheter body 70 can have a proximal end portion 72, a distal end portion 74, and a wall structure 82 that defines at least one injection channel 88 extending from the proximal end portion 72 toward the distal end portion 74. Optionally, in some aspects, the at least one injection channel 88 can comprise a single injection channel. Alternatively, in some aspects, the at least one injection channel 88 of the third catheter body 70 can comprise a plurality of injection channels. For example, in some aspects, the at least one injection channel 88 of the third catheter body 70 can comprise first and second injection channels 88. In these aspects, as shown in FIG. 3B, the wall structure 82 of the third catheter body 70 can comprise an outer wall 84 and an inner wall 86 that extends between opposing portions of the outer wall to define the first and second injection channels 88. As shown in FIG. 3D, the distal end portion 74 of the third catheter body 70 can further comprise at least one outlet opening 90 positioned in fluid communication with the at least one injection channel 88. Optionally, in some aspects, the at least one outlet opening 90 of the distal end portion 74 of the third catheter body 70 can comprise a plurality of outlet openings. In further optional aspects, the distal end portion 74 of the third catheter body 70 can comprises a static mixing component 76 positioned between the at least one injection channel 88 and the at least one outlet opening 90, as shown in FIG. 3D. As used herein, the term "static mixing component" does not require any particular structural arrangement. Rather, the "static mixing component" includes any in-line structure that promotes mixing of the materials delivered through the respective injection channels 88 as further disclosed herein. Optionally, the static mixing component 76 can be a housed-elements type static mixer, a plate-type static mixer, or combinations thereof. More generally, it is contemplated that the static mixing component 76 can have a central receiving channel that provides for a variable flow pathway between the at least one injection channel 88 and the at least one outlet opening 90. Such a variable flow pathway can be created by projections and recesses (changes in diameter) of the interior surfaces of the static mixing component, as well as the presence of obstructions that prevent portions of the injected materials from following a consistent axial path in a proximal-to-distal direction. It is understood that when only a single injection channel 88 is provided, or in other situations where mixing of injectable components is unnecessary prior to delivery, it is possible to omit the static mixing component from the third catheter body 70.

In further aspects, the distal end portion 74 of the third catheter body 70 can have a distal tip 78 and a diaphragm 80 that is secured to the distal tip. In these aspects, the diaphragm 80 can extend outwardly from the distal tip 78. It is contemplated that the diaphragm 80 of the third catheter body 70 can occlude the primary opening 52 of the second catheter body 40 to prevent entry of material into the primary opening of the second catheter body in a distal-to-proximal direction. For example, it is contemplated that the diaphragm can be biased and/or deformable to a blocking position in which the outer diameter of the diaphragm is greater than the diameter of the primary opening 52 of the second catheter body. It is further contemplated that the diaphragm 80 can comprise a flexible material that is deformable as the third catheter body 70 exits the second catheter body (upon initial deployment) or is received within the second catheter body (upon retraction of the third catheter body), with the diaphragm blocking the entry of material into the second catheter body. In exemplary aspects, and as shown in FIGS. 3A-3C, the diaphragm can be secured to the distal tip 78 and have a convex outer surface extending circumferentially around the distal tip, with a proximal portion of the diaphragm at least partially overlapping with the outlet openings 90 (moving in a distal-to-proximal direction). As the third catheter body continues to move in a proximal direction within the primary opening of the second catheter body, the proximal surface of the diaphragm can contact the portions of the second catheter body to thereby movement of the diaphragm to a fully blocking position. Prior to complete receipt of the third catheter body 70 within the primary opening 52 of the second catheter body 40, it is contemplated that the injection of material through the outlet openings of the third catheter body can displace other fluid within the delivery site (e.g., LAA), with the displaced fluid flowing into the primary opening of the second catheter body.

It is contemplated that the first, second, and third catheter bodies can be formed from a variety of materials. The materials can be selected such that the first, second, and third catheter bodies have structural integrity sufficient to permit advancement of each catheter body as described herein and permit maneuvering and operation of each catheter body, while also permitting yielding and bending in response to encountered anatomical barriers and obstacles within the subject's body (e.g., within the vasculature). In exemplary aspects, the first, second, and/or third catheter bodies can be formed front a material or combination of materials, such as polymers, metals, and polymer-metal composites. In some aspects, soft durometer materials can be used to form all or part of the respective catheter body to reduce discomfort and minimize the risk of damage to the subject's vasculature (e.g., perforation). In some embodiments, the first, second, and/or third catheter bodies can be formed, in whole or in part, from a polymeric material. Examples of suitable plastics and polymeric materials include, but are not limited to, silastic materials and silicon-based polymers, polyether block amides (e.g., PEBAX®, commercially available from Arkema, Colombes, France), polynnides, polyurethanes, polyaniides (e.g., Nylon 6,6), polyvinylchlorides, polyesters e.g., HYTREL®, commercially available from DuPont, Wilmington, Del.), polyethylenes (PE), polyether ether ketone (PEEK), fluoropolymers such as polytetrafluoroethylene (PTFE), perfluoroalkoxy, fluorinated ethylene propylene, or blends and copolymers thereof. Examples of suitable metals which can form some or all of the first, second, and/or third catheter bodies include stainless steel (e.g., 304 stainless steel), nickel and nickel alloys (e.g., nitinol or MP-35N), titanium, titanium alloys, and cobalt alloys. In certain embodiments, each catheter body can comprise two different materials. Radiopaque alloys, such as platinum and titanium alloys, may also be used to fabricate, in whole or in part, the delivery catheter to facilitate real-time imaging during procedures performed using the delivery catheter. Optionally, the first, second, and/or third catheter bodies can be coated or treated with various polymers or other compounds in order to provide desired handling or performance characteristics, such as to increase lubricity. In certain embodiments, the first, second, and/or third catheter bodies can be coated with polytetrafluoroethylene (PTFE) or a hydrophilic polymer coating, such as poly(caprolactone), to enhance lubricity and impart desirable handling characteristics.

In use, and with reference to FIGS. 5-11, the catheter assembly 10 disclosed herein can be deployed into the body of a subject as described below. While the following method is described with respect to the occlusion of a LAA, it is contemplated that the disclosed method steps can be applied to complete the occlusion of other openings, passageways, cavities, and channels within the body of a subject. The first catheter body 12 can be advanced through a first opening 104, such as an inter-atrial septum of a heart 100. It is contemplated that the first catheter body 12 can comprise a flexible material (e.g., a flexible material that is conventionally used for constructing catheters) permitting the first catheter body to conform to the shape of the passageways within the heart of the subject. Following such advancement through the first opening 104, the first balloon 30 can be selectively inflated to occlude the first opening 104. In exemplary aspects, the first balloon 30 can be positioned on a left atrial septal (e.g., distal) side 106 of the inter-atrial septum 104 of the heart 102 to prevent unintended withdrawal of the catheter assembly 10 back across the septum to the right atrium of the heart. In these aspects, the first balloon 30 can serve as an anchor holding the distal tip 18 of the first catheter 12 in the left atrium across the inter-atrial septum 104.

Figure 6:
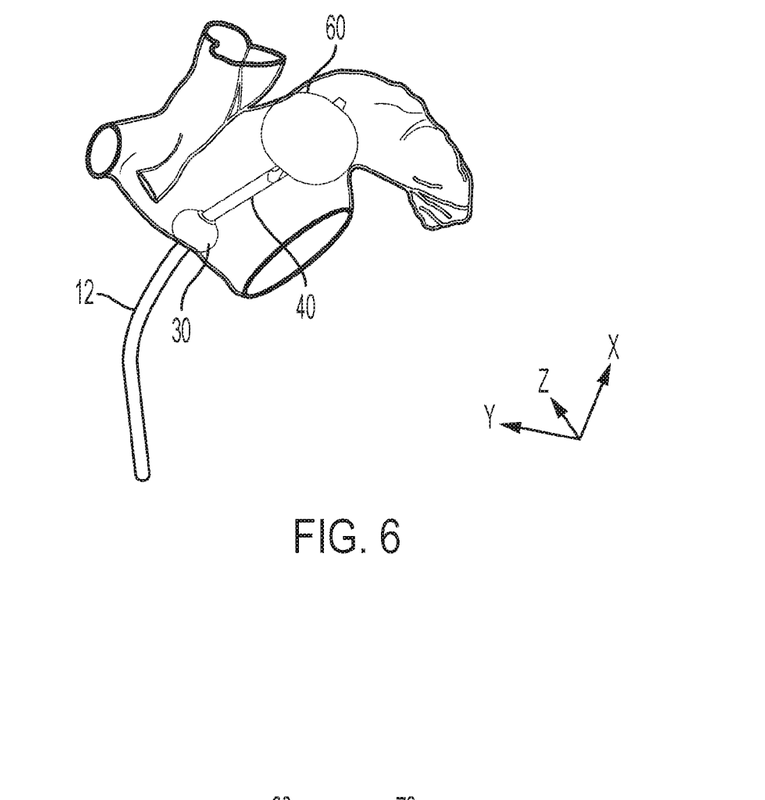
FIG. 6 is a perspective view depicting an exemplary catheter assembly, showing a second catheter body advanced relative to a first catheter body and a second balloon inflated and positioned proximally of the ostium of a left atrial appendage, as described herein.

After inflation of the first balloon 30, the second catheter body 40 can be selectively advanced relative to the first catheter body 12. It is contemplated that the second catheter body 40 can comprise a flexible material (e.g., a flexible material that is conventionally used for constructing catheters) permitting the second catheter body to conform to the shape of the passageways within the heart of the subject. It is contemplated that braiding of the second catheter body 40 can allow for stable forward force to be transmitted to the distal tip 46 of the second catheter body 40 and avoid bending, kinking, or collapse due to the force. Following advancement of the second catheter body 40, the second balloon 60 can be selectively inflated to occlude a second opening 108, such as an ostium of the LAA 110 of the heart 100. It is contemplated that the second balloon 60 can be positioned proximally of the ostium 108 of the LAA 110. By positioning the first balloon 30 on the left atrial septal side 106 of the inter-atrial septum 104 and the second balloon 60 proximally of the ostium 108 of the LAA 110, the first balloon can provide axial support for the secoond balloon to maintain occlusion of the LAA. As noted above, the second balloon 60 can be larger than the first balloon 30 and can fully occlude the LAA 110 at the ostium 108, thereby preventing exit of material from the LAA through the ostium. Additionally, the first catheter body 12 can be pulled in a proximal direction to press the first balloon 30 against the inter-atrial septum 104, and the second catheter body 40 can be pushed in a distal direction to press the second balloon 60 against the ostium 108 of the LAA 110. Optionally, the first and second catheter bodies 12, 40 can be locked in position prior to the step of advancing the third catheter body 70 relative to the second catheter body. By locking the first and second catheter bodies 12, 40 in the position, the force of pulling on the first balloon 30 against the inter-atrial septum 104 and pushing on the second balloon 60 against the ostium 108 of the LAA 110 can maintain occlusion of the LAA.

Figure 7:
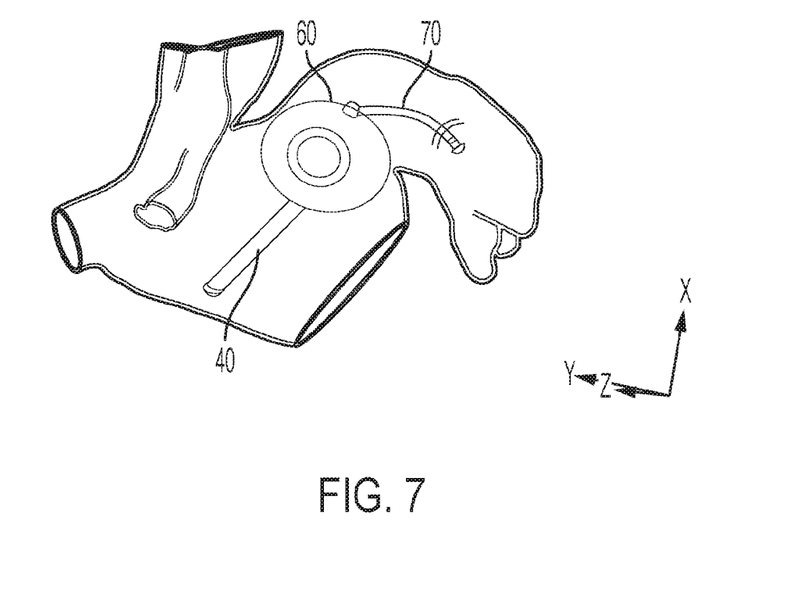
FIGS. 7-8 are perspective views depicting an exemplary catheter assembly, showing a third catheter body advanced relative to a second catheter body, as described herein.
Figure 8:
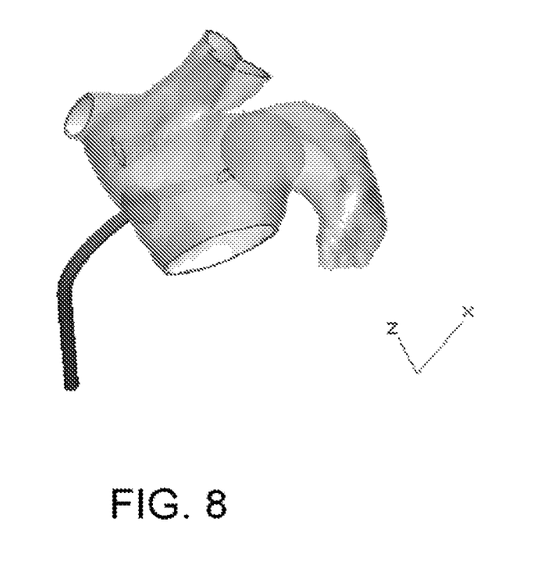

Following inflation of the second balloon 60, the third catheter body 70 can be selectively advanced relative to the second catheter body 40. It is contemplated that the third catheter body 70 can comprise a flexible material (e.g., a flexible material that is conventionally used for constructing catheters) permitting the third catheter body to conform to the anatomy of the LAA 110 and allow for delivery of at least one injectable material 200 to the LAA. After the third catheter body 70 is advanced relative to the second catheter body 40, the at least one injectable material 200 can be selectively delivered to the at least one injection channel 88 of the third catheter body 70. It is contemplated that the at least one injectable material 200 can comprise a bio-inert polymer material. Optionally, in some aspects, the at least one injectable material 200 can comprise a plurality of injectable polymer materials that are injected separately into respective injection channels 88 of the third catheter body 70. For example, the at least one injectable material 200 can comprise a pre-polymer material and a reagent for solidifying the pre-polymer material, and these materials can be injected separately through two respective injection channels of the third catheter body 70. The two injectable materials can then be delivered through respective injection channels 88 to the static mixer 76 of the third catheter body 70.

Figure 9:
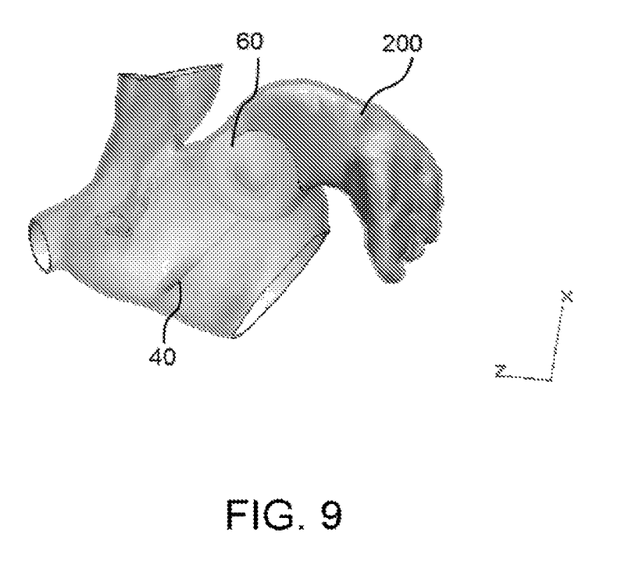
FIG. 9. is a perspective view depicting an exemplary catheter assembly, showing an injectable material delivered to the left atrial appendage of a heart, as described herein.
Figure 10:
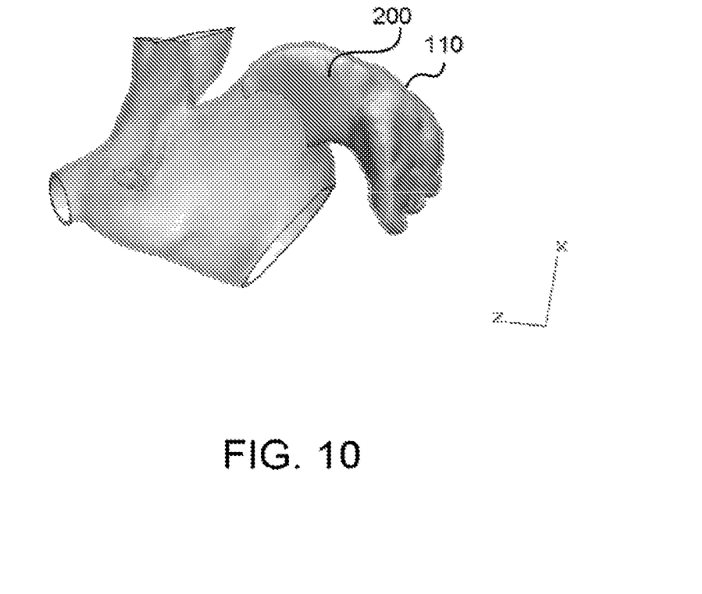
FIG. 10 is a perspective view of the heart of FIG. 9, showing the catheter assembly withdrawn from the heart, as described herein.
Figure 11:
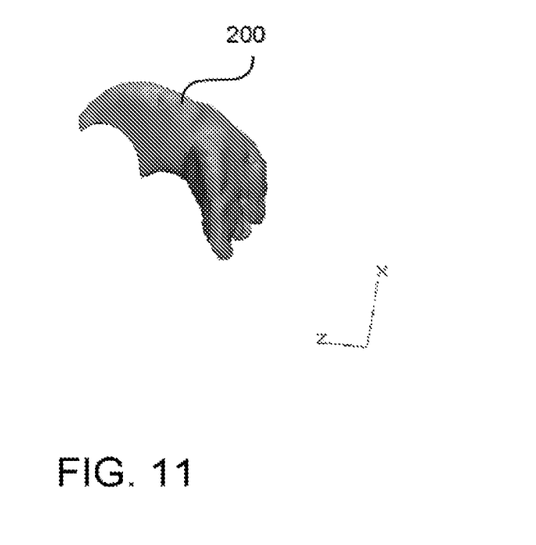
FIG. 11 is an isolated perspective view of the injectable material of FIG. 9, as described herein.

Once the at least one injectable material 200 passes through the third catheter body 70, the at least one injectable material 200 can be delivered to a selected delivery site 110, such as the LAA of the heart, through the at least one outlet opening 90 of the third catheter body 70. The third catheter body 70 can be configured to advance into the LAA 110. Following positioning of the distal end portion of the third catheter body within the LAA, the at least one injectable material 200 can be delivered to the LAA through the at least one outlet opening 90. The LAA will continue to be filled with the injectable material, and as the LAA fills up, the clinician can begin withdrawing the third catheter body from the LAA to provide more volume within the LAA for receipt of the injectable material. In exemplary aspects, the third catheter body can deliver the at least one injectable material 200 to the selected delivery site 110 (e.g., LAA) as the third catheter body 70 is withdrawn into the second catheter body 40. In these aspects, the third catheter body 70 can be withdrawn into the primary opening 52 of the second catheter body 40, and the at least one injectable material 200 can be delivered to the selected delivery site 110 through the at least one outlet opening 90 of the third catheter body 70 until the third catheter body is fully received within the primary opening 52 of the second catheter body 40. This continued delivery of material during the withdrawal of the third catheter body can maximize the volume of material delivered to the selected delivery site (e.g., LAA). In these aspects, the third catheter body 70 can be withdrawn until the third catheter body is fully received within the primary opening 52 of the second catheter body 40, and a diaphragm at the distal tip of the third catheter body can then occlude the primary opening of the second catheter body to prevent entry of material into the primary opening of the second catheter body in a distal-to-proximal direction. After the third catheter body 70 is received within the primary opening 52 of the second catheter body 40 and the diaphragm blocks further entry of material into the primary opening of the second catheter body, the second balloon 60 can be maintained in place until the at least one injectable material 200 is sufficiently hardened within the delivery site 110. In these aspects, the second balloon 60 and the diaphragm of the third catheter body 70 can occlude the second opening 108 and the primary opening 52 of the second catheter body 40 until the at least one injectable material 200 is sufficiently hardened within the delivery site 110. After the appropriate curing period has elapsed, the second and third catheter bodies 40, 70 can be removed and the first catheter body 12 can be used for final angiographic confirmation of LAA closure. Any injectable material 200 that remains in the respective injection channels 88 of the third catheter body 70 can be removed with the removal of the second and third catheter bodies 40, 70.

It is contemplated that the at least one injectable material 200 can be a crosslinkable biomaterial. It is further contemplated that any suitable biomaterial can be used. For example and without limitation, the biomaterial can be a crosslinkable biomaterial which is injected into the cavity or passageway (e.g., the LAA) in a fluid or gel form, and which crosslinks in situ, increasing in viscosity to form a biocompatible polymeric matrix. In these cases, the biocompatible polymeric matrix can function as an occlusive body, occupying the void space of the cavity or passageway. In the case of injection of a crosslinkable biomaterial into the LAA for purposes of occlusion, the biocompatible polymeric matrix can function as an occlusive body, occupying the void space of the LAA without adversely impacting cardiac function.

In the above description of the first, second, and third catheter bodies, reference is made to advancement or withdrawal of each catheter body. It is understood that such advancement and withdrawal of the catheter bodies can be accomplished using conventional surgical and diagnostic tools that are routinely used to initiate axial movement of a catheter within the body of a subject. In exemplary aspects, it is contemplated that the catheter assembly disclosed herein can comprise at least one handle assembly for steering and locking at least one of the catheter bodies as disclosed herein. In further exemplary aspects, it is contemplated that the first, second, and/or third catheter bodies can be configured to receive a guidewire and/or sheath to facilitate advancement of the respective catheter body, as further described below.

In use, and as further disclosed herein, the first (proximal) balloon can be designed to cross the interatrial septum and inflate and apply traction, thereby anchoring the first balloon in the left atrium to the left aspect of the interatrial septum. The second (distal) balloon can then be advanced through the lumen of the first (proximal) balloon and into the left atrium, where it is advanced to the ostium of the LAA and inflated, fully occluding the LAA at the level of the ostium. The locking mechanism can then be secured to lock the position of the two catheter bodies (and balloon assemblies) in this position. The third (delivery) catheter body can then be advanced into the lumen of the second catheter body until the third catheter body is within the occlude cavity of the LAA. This third catheter body is smaller than the lumen of the second catheter body such that liquid may pass into the lumen of the second (distal) balloon around the third catheter body. This third catheter body is advanced to the distal portion of the LAA. The polymer components are then injected into the third (delivery) catheter which displaces the liquid currently present in the LAA which drains into the lumen of the second catheter. As the polymer is injected into the LAA cavity, the third catheter body can be slowly withdrawn into the lumen of the second catheter body. When the cavity of the LAA is fully occupied by the injected mixed polymer, the third catheter body can be pulled to the distal orifice of the second catheter body, thereby completely occluding the distal balloon lumen with the diaphragm located at the distal tip of the third catheter body. After adequate time has elapsed for solidification of the delivered polymer, the second (distal) balloon is deflated and the second and third catheter bodies are removed together through the first (proximal) catheter body. The first (proximal) balloon is then deflated and the first balloon and the first catheter body are removed from the left atrium and removed from the body.

In exemplary aspects, it is contemplated that the catheter assembly can be coupled to an external port to facilitate access to the catheter assembly. In further aspects, it is contemplated that a proximal region of the catheter assembly (i.e., the proximal portion of the first catheter body) can include a manifold to facilitate access to the respective openings and/or channels of the first, second, and third catheter bodies. In these aspects, the catheter assembly can include a port for fluid connection to the at least one inflation channel, the at least one outlet opening, and/or the primary opening of the first catheter body, a port for fluid connection to the at least one inflation channel, the at least one outlet opening, and/or the primary opening of the second catheter body, and/or a port for fluid connection to the at least one injection channel and/or the at least one outlet opening of the third catheter body. In some embodiments, one or more of the ports, such as the port for fluid connection to the primary opening of the first catheter body, can be connected to a branched port (e.g., a hemostatic valve) to facilitate access of the opening by multiple devices or for multiple purposes (e.g., to advance a guidewire and monitor pressure). The ports can be configured to form leak-free connections (e.g., a Luer Taper connection such as a Luer-lock or Luer-slip connection) with, for example, indeflators and syringes used to inject fluid into the catheter bodies or to withdraw fluid from the catheter bodies(e.g., to inject the injectable material).

Exemplary Dimensions

In exemplary non-limiting aspects, it is contemplated that the length of the first (proximal) catheter body can range from about 60 cm to about 80 cm in length or from about 65 cm to about 75 cm in length, including a length of about 70 cm. In further non-limiting aspects, it is contemplated that the distal surface of the first (proximal) balloon can be spaced from the distal tip of the first catheter body by a distance of less than or equal to 30 mm, less than or equal to 20 mm, or, more preferably, about 15 mm. In still further non-limiting aspects, it is contemplated that the outer diameter of the first catheter body can optionally have a gauge ranging from 12 FR to 18 FR, or more particularly, a gauge of 14 FR or 15 FR. In still further non-limiting aspects, it is contemplated that the inflation openings of the first catheter body can have an outer diameter ranging from about 4 mm to about 6 mm (e.g., about 5 mm) measured relative to the axial length of the catheter.

In exemplary non-limiting aspects, it is contemplated that the length of the second catheter body can range from about 60 cm to about 90 cm in length or from about 65 cm to about 85 cm in length, including a length of about 75 cm. In further non-limiting aspects, it is contemplated that the distal surface of the second (distal) balloon can be spaced from the distal tip of the second catheter body by a distance of less than or equal to 10 cm, less than or equal to 7 cm, or, more preferably, about 5 cm. Optionally, the second (distal) balloon can have a length of about 3 cm, and the proximal surface of the second balloon can be spaced from the proximal end of the second catheter body by a distance ranging from about 50 cm to about 80 cm or from about 60 cm to about 70 cm, including about 67 cm. In still further non-limiting aspects, it is contemplated that the outer diameter of the second catheter body can optionally have a gauge ranging from 8 FR to 14 FR, or more particularly, a gauge of 10 FR or 11 FR. In still further non-limiting aspects, it is contemplated that the inflation openings of the first catheter body can have an outer diameter ranging from about 4 mm to about 6 mm (e.g., about 5 mm) measured relative to the axial length of the catheter.

In exemplary non-limiting aspects, it is contemplated that the length of the third catheter body can range from about 65 cm to about 90 cm or from about 75 cm to about 85 cm, including about 80 cm. Thus, in exemplary aspects, the third catheter body can have a greater length than the second catheter body, which can have a greater length than the first catheter body. Optionally, in these aspects, the third catheter body can be designed to extend from the distal end of the second catheter body by up to 5 cm, and the second catheter body can be designed to extend from the distal end of the first catheter body by up to 5 cm. In still further non-limiting aspects, it is contemplated that the outer diameter of the third catheter body can optionally have a gauge ranging from 5 FR to 11 FR, or more particularly, a gauge of 7 FR or 8 FR.

Exemplary Aspects

The following paragraphs describe exemplary, non-limiting aspects of the disclosed inventive concept.

Aspect 1: A catheter assembly comprising: a first catheter body having a proximal end portion, a distal end portion having a distal tip, and a wall that circumferentially encloses a primary opening, wherein the first catheter body further comprises at least one inflation channel within the wall of the first catheter body, wherein the primary opening of the first catheter body extends along an entire length of the first catheter body; a first balloon coupled to the distal end portion of the first catheter body and positioned in fluid communication with the at least one inflation channel of the first catheter body, the first balloon enclosing an interior space, wherein the first catheter body extends through the interior space of the first balloon in a proximal-to-distal direction such that at least the distal tip of the first catheter body is positioned distal of the first balloon; a second catheter body partially received within the primary opening of, and selectively moveable relative to, the first catheter body, wherein the second catheter body has a proximal end portion, a distal end portion having a tip, and a wall that circumferentially encloses a primary opening, wherein the second catheter body further comprises at least one inflation channel within the wall of the second catheter body, wherein the primary opening of the second catheter body extends along an entire length of the second catheter body; a second balloon coupled to the distal end portion of the second catheter body and positioned in fluid communication with the at least one inflation channel of the second catheter body, the second balloon enclosing an interior space, wherein the second catheter body extends through the interior space of the second balloon in the proximal-to-distal direction such that at least the distal tip of the second catheter body is positioned distal of the second balloon; and a third catheter body partially received within the primary opening of, and selectively moveable relative to, the second catheter body, wherein the third catheter body has a proximal end portion, a distal end portion, and a wall structure that defines at least one injection channel extending from the proximal end portion toward the distal end portion, wherein the distal end portion of the third catheter body further comprises at least one outlet opening positioned in fluid communication with the at least one injection channel.

Aspect 2: The catheter assembly of aspect 1, wherein the at least one injection channel of the third catheter body comprises a plurality of injection channels.

Aspect 3: The catheter assembly of aspect 1, wherein the at least one injection channel of the third catheter body comprises first and second injection channels, and wherein the wall structure of the third catheter body comprises an outer wall and an inner wall that extends between opposing portions of the outer wall to define the first and second injection channels.

Aspect 4: The catheter assembly of any one of aspects 1-3, wherein the at least one outlet opening of the distal end portion of the third catheter body comprises a plurality of outlet openings.

Aspect 5: The catheter assembly of any one of aspects 1-4, wherein the distal end portion of the third catheter body further comprises a static mixing component positioned between the at least one injection channel and the at least one outlet opening.

Aspect 6: The catheter assembly of any one of aspects 1-5, wherein, in an inflated position, the second balloon is larger than the first balloon.

Aspect 7: The catheter assembly of any one of aspects 1-6, wherein the wall of the first catheter body defines at least one outlet opening to provide fluid communication between the at least one inflation channel and the interior space of the first balloon.

Aspect 8: The catheter assembly of any one of aspects 1-7, wherein the wall of the second catheter body defines at least one outlet opening to provide fluid communication between the at least one inflation channel and the interior space of the second balloon.

Aspect 9: The catheter assembly of any one of aspects 1-8, wherein the distal end portion of the third catheter body has a distal tip and a diaphragm that is secured to the distal tip, the diaphragm extending outwardly from the distal tip.

Aspect 10: The catheter assembly of aspect 9, wherein the third catheter body is selectively retractable relative to the second catheter body, and wherein when the third catheter body is retracted to be fully received within the primary opening of the second catheter body, the diaphragm of the third catheter body occludes the primary opening of the second catheter body to prevent entry of material into the primary opening of the second catheter body in a distal-to-proximal direction.

Aspect 11: The catheter assembly of any one of aspects 1-10, wherein the second catheter body is selectively retractable relative to the first catheter body.

Aspect 12: The catheter assembly of any one of aspects 1-11, wherein the first and second catheter bodies are selectively lockable to maintain a desired position and orientation of the second catheter body relative to the first catheter body.

Aspect 13: A method comprising: deploying the catheter assembly of any one of aspects 1-12; selectively inflating the first balloon to occlude a first opening; selectively advancing the second catheter body relative to the first catheter body; selectively inflating the second balloon to occlude a second opening; selectively advancing the third catheter body relative to the second catheter body; selectively delivering at least one injectable material to the at least one injection channel of the third catheter body; and delivering the at least one injectable material to a selected delivery site through the at least one outlet opening of the third catheter body.

Aspect 14: The method of aspect 13, wherein the first opening is an inter-atrial septum of a heart, wherein the second opening is an ostium of a left atrial appendage of the heart, and wherein the selected delivery site is the left atrial appendage of the heart.

Aspect 15: The method of aspect 14, wherein the first balloon is positioned on a left atrial septal side of the inter-atrial septum, wherein the second balloon is positioned proximally of the ostium of the left atrial appendage, and wherein the first balloon provides axial support for the second balloon to maintain occlusion of the left atrial appendage.

Aspect 16: The method of aspect 15, further comprising: pulling the first catheter body in a proximal direction to press the first balloon against the inter-atrial septum; pushing the second catheter body in a distal direction to press the second balloon against the ostium of the left atrial appendage.

Aspect 17: The method of any one of aspects 13-16, further comprising withdrawing the third catheter body into the primary opening of the second catheter body.

Aspect 18: The method of aspect 17, wherein the at least one injectable material is delivered to the selected delivery site through the at least one outlet opening of the third catheter body until the third catheter body is fully received within the primary opening of the second catheter body.

Aspect 19: The method of aspect 17 or aspect 18, further comprising withdrawing the third catheter body until the third catheter body is fully received within the primary opening of the second catheter body, wherein a diaphragm secured to a distal tip of the third catheter body occludes the primary opening of the second catheter body to prevent entry of material into the primary opening of the second catheter body in a distal-to-proximal direction.

Aspect 20: The method of aspect 19, further comprising allowing the second balloon and the diaphragm of the third catheter body to occlude the second opening and the primary opening of the second catheter body until the at least one injectable material is sufficiently hardened within the delivery site.

Aspect 21: The method of any one of aspects 13-20, further comprising locking the first and second catheter bodies in position prior to the step of advancing the third catheter body relative to the second catheter body.

Aspect 22: The method of any one of aspects 13-21, wherein the at least one injectable material comprises a bio-inert polymer material.

Aspect 23: The method of any one of aspects 13-22, wherein the at least one injectable material comprises a plurality of injectable polymer materials that are injected separately into respective injection channels of the third catheter body.

Aspect 24: A catheter assembly as disclosed herein.

Aspect 25: A catheter assembly comprising a first catheter body and a first balloon as disclosed herein.

Aspect 26: A catheter assembly comprising a second catheter body and a second balloon as disclosed herein.

Aspect 27: A catheter assembly comprising a third catheter body as disclosed herein.

Aspect 28: A method of using the catheter assembly of any one of aspects 24-27.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A catheter assembly comprising:
a first catheter body having a proximal end portion, a distal end portion having a distal tip, and a wall that circumferentially encloses a primary opening, wherein the first catheter body further comprises at least one inflation channel within the wall of the first catheter body, wherein the primary opening of the first catheter body extends along an entire length of the first catheter body;
a first balloon coupled to the distal end portion of the first catheter body and positioned in fluid communication with the at least one inflation channel of the first catheter body, the first balloon enclosing an interior space, wherein the first catheter body extends through the interior space of the first balloon in a proximal-to-distal direction such that at least the distal tip of the first catheter body is positioned distal of the first balloon;
a second catheter body partially received within the primary opening of, and selectively moveable relative to, the first catheter body, wherein the second catheter body has a proximal end portion, a distal end portion having a tip, and a wall that circumferentially encloses a primary opening, wherein the second catheter body further comprises at least one inflation channel within the wall of the second catheter body, wherein the primary opening of the second catheter body extends along an entire length of the second catheter body;
a second balloon coupled to the distal end portion of the second catheter body and positioned in fluid communication with the at least one inflation channel of the second catheter body, the second balloon enclosing an interior space, wherein the second catheter body extends through the interior space of the second balloon in the proximal-to-distal direction such that at least the distal tip of the second catheter body is positioned distal of the second balloon; and
a third catheter body partially received within the primary opening of, and selectively moveable relative to, the second catheter body, wherein the third catheter body has a proximal end portion, a distal end portion, and a wall structure that defines at least one injection channel extending from the proximal end portion toward the distal end portion, wherein the distal end portion of the third catheter body further comprises at least one outlet opening positioned in fluid communication with the at least one injection channel,
wherein the distal end portion of the third catheter body has a distal tip and a diaphragm that is secured to the distal tip, the diaphragm extending outwardly from the distal tip, wherein the third catheter body is selectively retractable relative to the second catheter body, and wherein when the third catheter body is retracted to be fully received within the primary opening of the second catheter body, the diaphragm of the third catheter body occludes the primary opening of the second catheter body to prevent entry of material into the primary opening of the second catheter body in a distal-to-proximal direction.

2. The catheter assembly of claim 1, wherein the at least one injection channel of the third catheter body comprises a plurality of injection channels.

3. The catheter assembly of claim 1, wherein the at least one injection channel of the third catheter body comprises first and second injection channels, and wherein the wall structure of the third catheter body comprises an outer wall and an inner wall that extends between opposing portions of the outer wall to define the first and second injection channels.

4. The catheter assembly of claim 1, wherein the at least one outlet opening of the distal end portion of the third catheter body comprises a plurality of outlet openings.

5. The catheter assembly of claim 1, Wherein the distal end portion of the third catheter body further comprises a static mixing component positioned between the at least one injection channel and the at least one outlet opening.

6. The catheter assembly of claim 1, wherein, in an inflated position, the second balloon is larger than the first balloon.

7. The catheter assembly of claim 1, wherein the wall of the first catheter body defines at least one outlet opening to provide fluid communication between the at least one inflation channel and the interior space of the first balloon.

8. The catheter assembly of claim 1, wherein the wall of the second catheter body defines at least one outlet opening to provide fluid communication between the at least one inflation channel and the interior space of the second balloon.

9. The catheter assembly of claim 1, wherein the second catheter body is selectively retractable relative to the first catheter body.

10. The catheter assembly of claim 1, wherein the first and second catheter bodies are selectively lockable to maintain a desired position and orientation of the second catheter body relative to the first catheter body.

11. A method comprising:
deploying the catheter assembly of claim 1;
selectively inflating the first balloon to occlude a first opening;
selectively advancing the second catheter body relative to the first catheter body;
selectively inflating the second balloon to occlude a second opening;
selectively advancing the third catheter body relative to the second catheter body;
selectively delivering at least one injectable material to the at least one injection channel of the third catheter body; and
delivering the at least one injectable material to a selected delivery site through the at least one outlet opening of the third catheter body.

12. The method of claim 11, wherein the first opening is an inter-atrial septum of a heart, wherein the second opening is an ostium of a left atrial appendage of the heart, and wherein the selected delivery site is the left atrial appendage of the heart.

13. The method of claim 12, wherein the first balloon is positioned on a left atrial septal side of the inter-atrial septum, wherein the second balloon is positioned proximally of the ostium of the left atrial appendage, and wherein the first balloon provides axial support for the second balloon to maintain occlusion of the left atrial appendage.

14. The method of claim 13, further comprising:
pulling the first catheter body in a proximal direction to press the first balloon against the inter-atrial septum; and
pushing the second catheter body in a distal direction to press the second balloon against the ostium of the left atrial appendage.

15. The method of claim 11, further comprising withdrawing the third catheter body into the primary opening of the second catheter body.

16. The method of claim 15, wherein the at least one injectable material is delivered to the selected delivery site through the at least one outlet opening of the third catheter body until the third catheter body is fully received within the primary opening of the second catheter body.

17. The method of claim 15, further comprising withdrawing the third catheter body until the third catheter body is fully received within the primary opening of the second catheter body, wherein a diaphragm secured to a distal tip of the third catheter body occludes the primary opening of the second catheter body to prevent entry of material into the primary opening of the second catheter body in a distal-to-proximal direction.

18. The method of claim 17, further comprising allowing the second balloon and the third catheter body to occlude the second opening and the primary opening of the second catheter body until the at least one injectable material is sufficiently hardened within the delivery site.

19. The method of claim 11, further comprising locking the first and second catheter bodies in position prior to the step of advancing the third catheter body relative to the second catheter body.

20. The method of claim 11, wherein the at least one injectable material comprises a bio-inert polymer material.

21. The method of claim 11, wherein the at least one injectable material comprises a plurality of injectable polymer materials that are injected separately into respective injection channels of the third catheter body.

* * * * *